United States Patent
Ahearn et al.

(10) Patent No.: US 7,390,631 B2
(45) Date of Patent: Jun. 24, 2008

(54) DIAGNOSIS AND MONITORING OF SYSTEMIC LUPUS ERYTHEMATOSUS AND OF SCLERODERMA

(75) Inventors: Joseph M. Ahearn, Sewickley, PA (US); Susan M. Manzi, Wexford, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 560 days.

(21) Appl. No.: 10/489,219

(22) PCT Filed: Sep. 9, 2002

(86) PCT No.: PCT/US02/28910

§ 371 (c)(1),
(2), (4) Date: Mar. 10, 2004

(87) PCT Pub. No.: WO03/022223

PCT Pub. Date: Mar. 20, 2003

(65) Prior Publication Data

US 2005/0037441 A1 Feb. 17, 2005

Related U.S. Application Data

(60) Provisional application No. 60/318,541, filed on Sep. 10, 2001.

(51) Int. Cl.
*G01N 33/00* (2006.01)
(52) U.S. Cl. .............. 435/7.25; 435/7.1; 435/7.21; 435/372; 435/287.2; 435/967; 435/973; 436/507; 436/520; 436/546; 436/548; 436/10; 436/63; 436/172; 436/811; 436/821; 422/61

(58) Field of Classification Search .............. 435/7.1, 435/973, 7.21, 7.25, 7.92, 40.51, 337, 372, 435/287.2, 967; 436/507, 519, 520, 546, 436/548, 10, 63, 172, 811, 821; 422/61
See application file for complete search history.

(56) References Cited

U.S. PATENT DOCUMENTS 5,426,029 A * 6/1995 Rittershaus et al. ........ 435/7.21
2005/0042602 A1 2/2005 Ahearn et al.

FOREIGN PATENT DOCUMENTS

WO    WO 94/10571 A1    5/1994
WO    WO 03/022223 A2    3/2003

OTHER PUBLICATIONS

Freysdottir et al., A flow cytometric assay for measuring complement receptor 1 (CR1) and complement component C4d on erythrocytes, Journal of Immunological Methods 142: 45-52 (1991).*

(Continued)

*Primary Examiner*—Gailene R Gabel
(74) *Attorney, Agent, or Firm*—Gwendolyn R. Acker Wood; Eckert Seamans Cherin & Mellott, LLC

(57) ABSTRACT

Methods for diagnosing and monitoring systemic lupus erythematosus (SLE) or scleroderma by determining, in a blood sample from the individual being diagnosed or monitored, complement component C4d deposited on surfaces of red blood cells in the sample, and optionally also determining complement receptor CR1 deposited on the red blood cell surfaces. For diagnosis this is compared with the quantity of C4d (and optionally CR1) present on red blood cells of normal individuals. For monitoring it is compared with a value in a sample or samples previously obtained from the individual patient. The comparison may be made with individual values for C4d and CR1 and/or with a ratio of the two found in normal individuals.

21 Claims, 7 Drawing Sheets

OTHER PUBLICATIONS

Sirois et al., An Enzyme-Linked Immunosorbent Assay for the Detection of Complement Components on Red Blood Cells, Am. Journ. Clin. Path. 82 (1): 67-73 (Jul. 1984).*

Jouvin et al., Decreased Expression of C3b Receptor (CR1) on Erythrocytes of Patients with Systemic Lupus Erythematosus Contrasts with its Normal Expression in Other Systemic Diseases and Does Not Correlate with the Occurrence of Severity of SLE Nephritis, Complement 3: 88-96 (1986).*

Ross et al., Disease-Associated Loss of Erythocyte Complement Receptors (CR1) in Patients with Systemic Lupus Erythematosus and Other Diseases involving Autoantibodies and/or Complement Activation, The Journal of Immunology, vol. 135 (3): 2005-2013 (Sep. 1985).*

Lach-Trifilieth et al., Complement Receptor 1 (CD35 or CR1) on Human Reticulocytes: Normal Expression in Systemic Lupus Erythematosus and HIV-Infected Patients, The Journal of Immunology 162: 7549-7554 (1999).*

Buyon et al., Assessment of Disease Activity and Impending Flare in Patients with Systemic Lupus Erythematosus, Arthritis and Rheumatism, vol. 35, No. 9 (Sep. 1992).*

Ross et al., Disease-Associated Loss of Erythrocyte Complement Receptors (CR1) in Patients with Systemic Lupus Erythematosus and Other Diseases involving Autoantibodies and/or Complement Activation, The Journal of Immunology, vol. 135 (3): 2005-2013 (Sep. 1985).*

Buyon et al., Assessment of Disease Activity and Impending Flare in Patients with Systemic Lupus Erythematosus, Arthritis and Rheumatism, vol. 35, No. 9 (Sep. 1992).*

Jouvin, Marie-Helene et al.; "Decreased Expression of C3b Receptor (CR1) on Erythrocytes of Patients with Systemic Lupus erythematosus Contrasts with its Normal Expression in Other Systemic Diseases and Does Not Correlate with the Occurrence or Severity of SLE Nephritis"; *Complement* 1986, vol. 3, pp. 88-96.

McGeer, P.L. et al.; "Reactions of the Immune System in Chronic Degenerative Neurological Diseases"; *The Canadian Journal of Neurological Sciences* 1991, vol. 18, pp. 376-379.

Tausk, Francisco et al.; "The Expression of C3b Receptors in the Differentiation of Discoid Lupus Erythematosus and Systemic Lupus Erythematosus"; *Arthritis and Rheumatism* 1990, vol. 33, No. 6, pp. 888-892.

Tsuboi, Y. et al.; "Increased concentration of C4d complement protein in CSF in amyotrophic lateral sclerosis"; *Neurosurgery and Psychiatry* 1994, vol. 57, pp. 859-861.

Yamada, T. et al.; "Complement-activated oligodendroglia: a new pathogenic entity identified by immunostaining with antibodies to human complement proteins C3d and C4d"; *Neuroscience Letters* 1990, vol. 112, pp. 161-166.

Corvetta, Angelo et al.; "Low Number of Complement C3b/C4b Receptors (CR1) on Erythrocytes from Patients with Essential Mixed Cryoglobulinemia, Systemic Lupas Erythematosus and Rheumatoid Arthritis: Relationship with Disease Activity, Anticardiolipin Antibodies, Complement Activation and Therapy"; 1981, *J. Rheumatol.*, vol. 18, pp. 1021-1025.

Freysdottir, Jona et al.; "A flow cytometric assay for measuring complement receptor 1 (CR1) and the complement fragments C3d and C4d on erythrocytes"; 1991, *Journal of Immunological Methods*, vol. 142, pp. 45-52.

Manzi, Susan et al.; "Sensitivity and Specificity of Plasma and Urine Complement Split Products as Indicators of Lupus Disease Activity"; 1996, *Arthritis & Rheumatism*, vol. 39, No. 7, pp. 1178-1188.

Manzi, Susan et al.; "New insights into complement: a mediator of injury and marker of disease activity in systemic lupus erythematosus"; 2004, *Lupus*, vol. 13, pp. 1-6.

Ross, Gordon D. et al.; "Disease-Associated Loss of Erythrocyte Complement Receptors ($CR_1$, C3b Receptors) in Patients with Systemic Lupus Erythematosus and other Diseases Involving Autoantibodies and/or Complement Activation"; 1985, *Journal of Immunology*, vol. 135, No. 3, pp. 2005-2014.

Alexander, Elaine, et al., "*Serum complement activation in central nervous system disease in sjogren's syndrome*;" The American Journal of Medicine, Oct. 1988, vol. 85, No. 4, abstract only.

Atkinson, J.P., et al., "*Origin of the Fourth Component of Complement Related Chido and Rodgers Blood Group Antigens;*" 1988; Compliment; vol. 5; pp. 65-76.

Bombardier, Claire, et al., "*Derivation of the SLEDAI A Disease Activity Index for Lupus Patients;*" Arthritis Rheum, Jun. 1992, vol. 35; No. 6; pp. 630-640.

Buyon, J.P., et al., "*Assessment of disease activity and impending flare in patients with systemic lupus erythematosus;*" Arthritis Rheum, 1992, vol. 35, pp. 1028-1037.

Chudwin, D., et al., "*Activation of the Alternative Complement Pathway by Red Blood Cells from Patients with Sickle Cell Disease;*" Clinical Immunology and Immunopathology, May 1994, vol. 71, No. 2, pp. 199-202.

Cosio, F.G., et al., "*The high prevalence of severe early post-transplant renal allograft pathology in hepatitis C positive recipients;*" Transplantation, Oct. 27, 1996, vol. 62, No. 8, abstract only.

Falk, R.J.., et al., "*Radioimmunoassay of the attack complex of complement in serum from patients with systemic lupus erythematosus;*" N. Engl. J. Med., 1985, vol. 312, pp. 1594-1599.

Lach-Trifilieff, Estelle, et al., "*Complement Receptor 1 (CD35) on Human Reticulocytes: Normal Express in Systemic Lupus Erythematosus and HIV-Infected Patients;*" The Journal of Immunology, vol. 162, No. 12, Jun. 1999, pp. 7549-7554.

Lamprecht, P., et al., "*Immunological and clinical follow up of hepatitis C virus associated cryoglobulinaemic vasculitis;*" Annals of the Rheumatic Diseases, Apr. 2001, vol. 60, pp. 385-390.

Lian, Matthew H., et al., "*Reliability and Validity of Six Systems for the Clinical Assessment of Disease Activitity in Systemic Lupus Erythematosus,*" Arthritis Rheum, Sep. 1989, vol. 32; No. 9; pp. 1107-1118.

Manzi, Susan, et al.; "*Measurement of Erythrocyte C4d and Complement Receptor 1 in Systemic Lupus Erythematosus;*" Nov. 2004, Arthritis & Rheumatism, vol. 50, No. 11, pp. 3596-3604.

Accn. No. 85046338 Medline, McCarthy, T., et al., "*Intrauterine devices and pelvic inflammatory disease;*" Australian and New Zealand Journal of Obstretics and Gynecology, May 1984, vol. 24, No. 2, pp. 106-110, Abstract.

Accn. No. 90367342 Medline. Meliconi, R., et al., "*Complement activation products in idiopathic pulmonary fibrosis: relevance of fragment Ba to disease severity;*" Clinical Immunology and Immunopathology, Oct. 1990, vol. 57, No. 1, pp. 64-73, Abstract.

Navratil, J.S., et al., "*Apoptosis and autoimmunity: complement deficiency and systemic lupus erythematosus revisited;*" Curr. Rheumatol. Rep., 2000, vol. 2, pp. 32-38.

Ricker, D.M., et al., "*Serum C3 levels are diagnostically more sensitive and specific for systemic lupus erythematosus activity than are serum C4 levels;*" The Lupus Nephritis Collaborative Study Group, Am. J. Kidney Dis., 1991, vol. 18, pp. 678-685.

Senaldi, G., et al., "*Correlation of the activation of the fourth component of complement (C4) with disease activity in systemic lupus erythematosus;*" Ann. Rheum. Dis., 1988, vol. 47, pp. 913-917.

Sirois, M., et al., "*An Enzyme-linked Immunosorbent Assay for the Detection of Complement Components on Red Blood Cells;*" Am. Journ. Clin. Path., Jul. 1984, vol. 82, No. 1, pp. 67-73.

Tilley, C.A., et al., "*Localisation of Chido and Rodgers Determinants to the C4d Fragment of Human C4;*" Nature; Dec. 14, 1978; vol. 276, pp. 713-715.

* cited by examiner

DIAGNOSIS AND MONITORING OF SYSTEMIC LUPUS ERYTHEMATOSUS AND OF SCLERODERMA

CROSS REFERENCE TO RELATED APPLICATIONS

This application is a continuation-in-part of U.S. Provisional Application No. 60/318,541, filed Sep. 10, 2001, which is herein incorporated by reference.

FEDERALLY SPONSORED RESEARCH OR DEVELOPMENT

Certain work described herein was supported by Grant No. N01AR92239 between the NIH and University of Pittsburgh. The Government may have certain rights in this invention.

FIELD OF THE INVENTION

This invention relates to the diagnosis and/or monitoring of patients with systemic lupus erythematosus or scleroderma, including methods and kits for carrying out this activity.

BACKGROUND OF THE INVENTION

This invention relates to the diagnosis and/or monitoring of patients with systemic lupus erythematosus (SLE) and with systemic sclerosis (scleroderma). The invention also provides means for distinguishing between the two diseases and helps doctors distinguish SLE and scleroderma from other diseases.

Systemic lupus erythematosus (SLE) or lupus is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition causes chronic inflammation and tissue damage.

Diagnosing and monitoring disease activity are both problematic in patients with SLE. Diagnosis is problematic because the spectrum of disease is broad and ranges from subtle or vague symptoms to life threatening multi-organ failure. There are other diseases with multi-system involvement that can be mistaken for systemic lupus, or vice versa. Criteria were developed for the purpose of disease classification in 1971 (Cohen, AS, et al., 1971, Preliminary criteria for the classification of systemic lupus erythematosus. *Bull Rheum Dis* 21:643-648) and revised in 1982 (Tan, EM, et al., 1982. The 1982 revised criteria for the classification of systemic lupus erythematosus. *Arth Rheum* 25:1271-1277.) and 1997 (Hochberg, MC. 1997. Updating the American College of Rheumatology revised criteria for the classification of systemic lupus erythematosus. *Arth Rheum* 40:1725). These criteria are meant to ensure that patients from different geographic locations are comparable. Of the eleven criteria, the presence of four or more, either serially or simultaneously, is sufficient for classification of a patient as having SLE. Although the criteria serve as useful reminders of those features that distinguish lupus from other related autoimmune diseases, they are unavoidably fallible. Determining the presence or absence of the criteria often requires interpretation. If liberal standards are applied for determining the presence or absence of a sign or symptom, one could easily diagnose a patient as having lupus when in fact they do not. Similarly, the range of clinical manifestations in SLE is much greater than that described by the eleven criteria and each manifestation can vary in the level of activity and severity from one patient to another. To further complicate a difficult diagnosis, symptoms of SLE continually evolve over the course of the disease. New symptoms in previously unaffected organs can develop over time. There is no definitive test for lupus and, thus, it is often misdiagnosed.

Monitoring disease activity is also problematic in caring for patients with lupus. Lupus progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of lupus include hair loss, ulcers of mucous membranes and inflammation of the lining of the heart and lungs which leads to chest pain. Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in lupus, premature strokes and heart disease are not uncommon. Over time, however, these flares can lead to irreversible organ damage. In order to minimize such damage, earlier and more accurate detection of disease flares would not only expedite appropriate treatment, but would reduce the frequency of unnecessary interventions. From an investigative standpoint, the ability to uniformly describe the "extent of inflammation" or activity of disease in individual organ systems or as a general measure is an invaluable research tool. Furthermore, a measure of disease activity can be used as a response variable in a therapeutic trial.

Two of the most commonly used instruments are the Systemic Lupus Disease Activity Index (SLEDAI) (Bombardier, C., D. D. Gladman, et al. (1992). Derivation of the SLEDAI. A disease activity index for lupus patients. The Committee on Prognosis Studies in SLE. *Arth Rheum* 35: 630-40), and the Systemic Lupus Activity Measure (SLAM) (Liang, M. H., S. A. Socher, et al. (1989). Reliability and validity of six systems for the clinical assessment of disease activity in systemic lupus erythematosus. *Arth Rheum* 32: 1107-18). The SLEDAI includes 24 items representing 9 organ systems. The variables are obtained by history, physical examination and laboratory assessment. Each item is weighted from 1 to 8 based on the significance of the organ involved. For example, mouth ulcers are scored as 2, while seizures are scored as 8. The laboratory parameters that are included in the SLEDAI include white blood cell count, platelet count, urinalysis, serum C3, C4 and anti-dsDNA. The total maximum score is 105. The SLAM includes 32 items representing 11 organ systems. The items are scored not only as present/absent, but graded on a scale of 1 to 3 based on severity. The total possible score for the SLAM is 86. Both the SLEDAI and the SLAM have been shown to be valid, reliable, and sensitive to change over time (Liang, M. H., S. A. Socher, et al. (1989). Reliability and validity of six systems for the clinical assessment of disease activity in systemic lupus erythematosus. *Arth Rheum* 32:1107-18), and are widely used in research protocols and clinical trials. These indices are particularly useful for examining the value of newly proposed serologic or inflammatory markers of disease activity in SLE.

Despite the obvious utility of these instruments, there are some drawbacks. First, there is not always complete agreement between the SLAM and the SLEDAI in the same set of patients. There are several possible reasons for these discrepancies. Unlike the SLEDAI, the SLAM includes constitutional symptoms such as fatigue and fever, which may or may not be considered attributable to active SLE; this activity index relies on physician interpretation. In addition, the SLEDAI does not capture mild degrees of activity in some organ systems and does not have descriptors for several types of activity such as hemolytic anemia. For these and other reasons, most studies incorporate more than one measure of disease activity.

A general review of the state of the art can be found in Ramsey-Goldman, R. and Manzi, S. Systemic Lupus Erythematosus. In: Goldman and Hatch, Ed. Women and Health. Academic Press, San Diego, Calif. 2000: 704-723.

Systemic sclerosis (scleroderma) is a chronic disorder of connective tissue characterized by inflammation and fibrosis and by degenerative changes of the blood vessels, skin, gastrointestinal tract, lung, heart and kidney. Scleroderma is a disabling and life-threatening disease. Criteria have been developed for the classification of patients with scleroderma (Masi AT, Rodnan GP, Medsger TA Jr, et al. Preliminary criteria for the classification of systemic sclerosis (scleroderma). *Arth Rheum* 1980; 23:581-590). These criteria are intended for description of large series of patients in research studies and not for diagnosis of individual patients. The major criterion is sclerodermatosus skin changes (thickening of the skin) in any location proximal to the digits. With the addition of any two or three minor criteria [sclerodactyly (skin thickening involving the digits), digital pitting scars, bibasilar pulmonary interstitial fibrosis] the sensitivity for the diagnosis increases. However, nearly 10% of individuals with definite scleroderma do not satisfy these criteria (Medsger T A Jr. Comment on scleroderma criteria cooperative study. In: Black C M,. Myers A R, eds. Current Topics in Rheumatology: Systemic Sclerosis. New York: Gower Medical Publishing, 1985:16-17).

The status of a scleroderma patient or "severity" of his/her disease at a given time represents some combination of irreversible changes or "damage" and potentially reversible changes or "activity." Inflammation, early in the course of disease, leads to fibrosis and scarring later. If one could accurately detect the inflammatory activity, early intervention may prevent future irreversible damage. However, it is often difficult for clinicians to distinguish disease damage from disease activity. In part, this may be because clinical evidence of activity can be extremely subtle. In addition, there is no reliable laboratory marker of inflammation. Cross-sectional and longitudinal assessment of disease damage and activity are essential in evaluating the natural history of disease and in measuring the effectiveness of interventions, both in individual patients and in clinical trials. A review of this disorder can be found in Medsger T A Jr. Systemic sclerosis (scleroderma): clinical aspects. In: Koopman W J, ed. Arthritis and Allied Conditions. 13th ed. Philadelphia: Lea and Febiger, 1997: 1433-1464.

The complement system consists of a complex network of more than 30 functionally linked proteins that interact in a highly regulated manner to provide many of the effector functions of humoral immunity and inflammation, thereby serving as the major defense mechanism against bacterial and fungal infections. This system of proteins acts against invasion by foreign organisms via three distinct pathways: the classical pathway (in the presence of antibody) or the alternative pathway (in the absence of antibody) and the lectin pathway. Once activated, the proteins within each pathway form a cascade involving sequential self-assembly into multimolecular complexes that perform various functions intended to eradicate the foreign antigens that initiated the response.

The classical pathway is usually triggered by an antibody bound to a foreign particle. It consists of several components that are specific to the classical pathway and designated C1, C4, C2, (in that order in the pathway).

In the classical pathway, the first component C1q is bound to an antigen-antibody complex, activating the pathway. This event is followed by sequential activation of the two serine proteases C1r and C1s. Activated C1s has two substrates, the final two proteins of the classical pathway, namely C4 and C2. Protein C4 is cleaved into C4a and C4b. Protein C2 is cleaved to form C2a and C2b. Fragments C4b and C2a assemble to form C4b2a, which cleaves protein C3 into C3a and C3b, which completes activation of the classical pathway.

Fragments C4b and C3b are subject to further degradation by Factor I. This factor cleaves C4b to generate C4d and also cleaves C3b, to generate iC3b followed by C3d. Thus, activation of the classical pathway of complement can lead to deposition of a number of fragments, including C4d and iC3b on immune complexes or other activating surfaces. These fragments are ligands for complement receptor type 1 (CR1) on erythrocytes or red blood cells.

There have been inconsistent reports regarding complement proteins and SLE. One manifestation that has been reported in patients having SLE is a diminished expression of the complement receptor CR1 on erythrocytes [E-CR$_1$] as compared to normal individuals. This has been reported, for example, by Ross et al., J. Immunol., Vol. 135, p. 2005 (1985), Corvetta et al., J. Rheumatol., Vol. 18, 1021 (1991) and by others. Other studies seem to show there is no correlation. Iida et al., *J. Exp. Med*. 155, 1427 (1982) noted that the CR1 number on erythrocytes varied inversely with disease activity, with lower numbers occurring during periods of most severe manifestations of SLE, and higher numbers being observed during periods of remission in the same patients.

BRIEF SUMMARY OF THE INVENTION

The invention involves the use of determinations of complement component C4d, and of complement receptor CR1, a receptor present on the surfaces of erythrocytes that acts as a receptor for proteolytic fragments of C4 and C3.

In one aspect, this invention comprises a method of diagnosing systemic lupus erythematosus in an individual, comprising (a) determining, in a blood sample from the individual containing red blood cells, complement component C4d deposited on surfaces of red blood cells in the sample, and (b) comparing said determination with the quantity of component C4d deposited on the surface of red blood cells of individuals not having systemic lupus erythematosus.

In a second aspect, this invention comprises a method of monitoring systemic lupus erythematosus in an individual, comprising (a) determining, in a blood sample from the individual containing red blood cells, complement component C4d deposited on surfaces of red blood cells in the sample, and (b) comparing said determination with the quantity of component C4d deposited on the surface of red blood cells previously obtained from the individual.

In another aspect, this invention comprises a method of diagnosing scleroderma in an individual comprising (a) determining, in a blood sample containing red blood cells from the individual, complement component C4d deposited on surfaces of red blood cells in the sample, and (b) comparing the determination of said component with the quantity of said component known to be present on the surface of red blood cells of individuals not having scleroderma.

The invention further comprises a method of monitoring scleroderma in an individual, comprising (a) determining, in a blood sample from the individual containing red blood cells, complement component C4d deposited on surfaces of red blood cells in the sample, and (b) comparing said determination with the quantity of component C4d deposited on the surfaces of red blood cells previously obtained from the individual.

In preferred aspects of this invention, the method also includes determining complement receptor CR1 on the surfaces of red blood cells in the sample and comparing that determination with the quantity of CR1 present on the surfaces of red blood cells of patients not having SLE or scleroderma, respectively.

In other preferred aspects of this invention, the ratio of C4d to CR1 on surfaces of red blood cells is determined and compared with that of patients not having SLE or scleroderma, respectively, or if monitoring of a patient is being conducted, that ratio is compared with such a ratio previously determined for the patient (or for cells previously obtained from the patient).

In another preferred aspect of this invention, the method also includes determining complement receptor CR1 on the surfaces of red blood cells in the sample, and comparing said determinations with the quantity of CR1 deposited on the surfaces of red blood cells previously obtained from individuals with systemic lupus erythematosus and scleroderma respectively as a method of monitoring disease activity.

The invention also comprises automated methods of the above types, computer software for performing such automated methods, and kits for performing the methods described herein.

BRIEF DESCRIPTION OF THE DRAWINGS

FIG. 1 is a graphical depiction of levels of complement component C4d and complement receptor CR1 on the red blood cells of healthy individuals, i.e. those not having systemic lupus erythematosus, scleroderma or other known diseases.

FIG. 2 is a graphical depiction of levels of complement component C4d and complement receptor CR1 on the red blood cells of patients diagnosed as having systemic lupus erythematosus.

DETAILED DESCRIPTION OF THE INVENTION

General Discussion

Figure 1A:
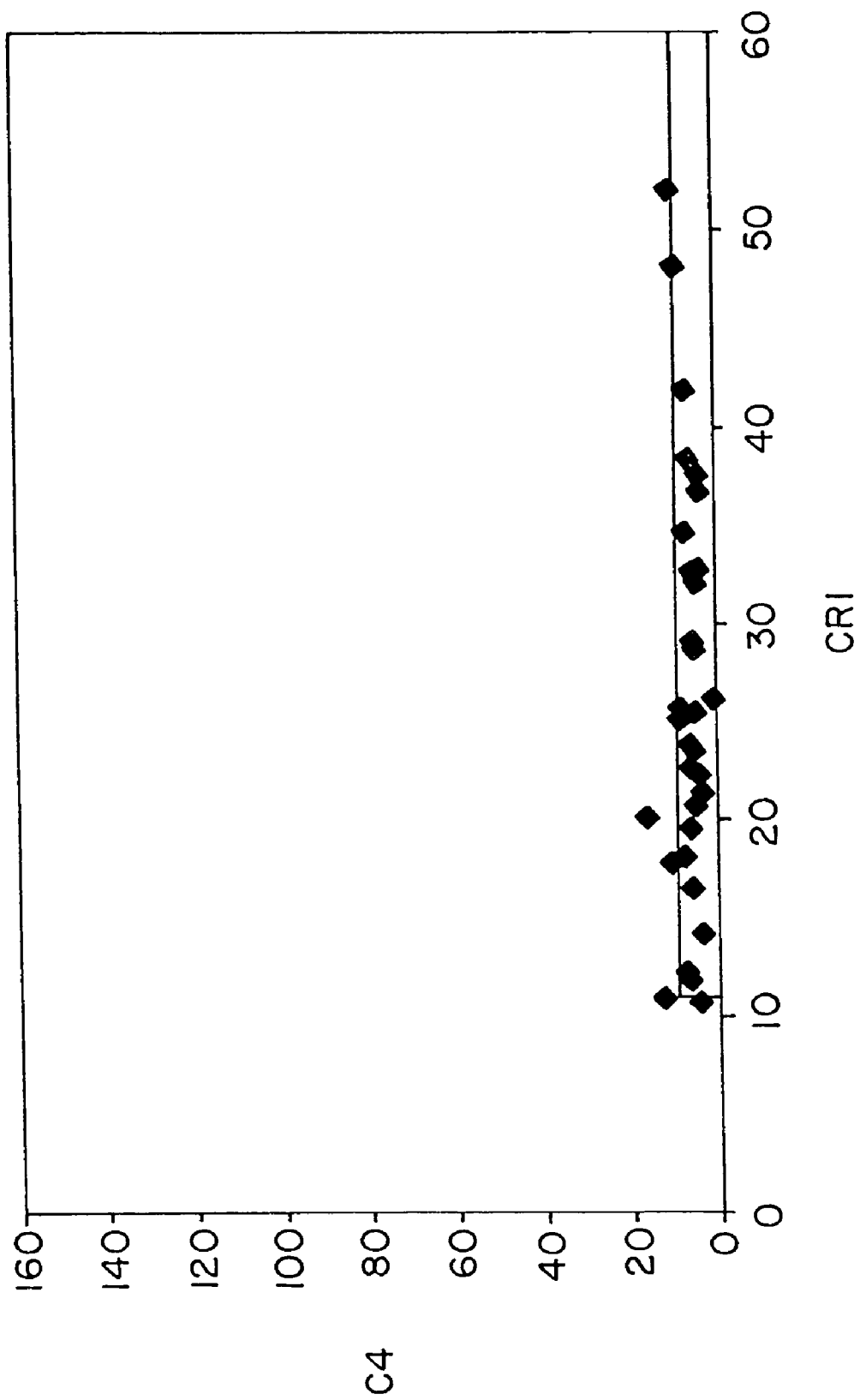
FIGS. 1a and 1b show the same data depicted using two different Y-axes. C4d and CR1 cutpoints, used to differentiate these healthy controls from patients with SLE, are shown.

The methods of this invention enable the diagnosis and/or monitoring of SLE and scleroderma. Because these two conditions are serious health problems, there is a need for relatively accurate and early diagnosis of these conditions. Likewise, the ability to monitor the activity of these diseases is of great importance.

The invention involves the use of determinations of complement component C4d and/or complement receptor CR1, a receptor present on the surfaces of erythrocytes that acts as a receptor for proteolytic fragments of C3 and C4.

In the most general sense, the methods of this invention are based on the discovery by the inventors that a determination of C4d deposited on surfaces of red blood cells of a patient can serve as a diagnostic marker for either SLE or scleroderma. As will be discussed below, a combination of this determination with a determination of CR1 expressed on surfaces of red blood cells of the same patient can aid in distinguishing between SLE and scleroderma as well as helping doctors distinguish between the two diseases and other diseases having similar manifestations.

In diagnosing the occurrence, or previous occurrence, of either disease, complement component C4d deposited on surfaces of red blood cells in a sample is determined. Complement receptor CR1 on the surfaces of the same red blood cells is preferably also determined. One or both of these determinations is then compared with the quantities of C4d and CR1, respectively, usually found on the surfaces of red blood cells of individuals not having SLE or scleroderma.

In monitoring disease activity of a patient with either disorder, the same determinations are made in the patient's blood sample, and are then compared with determinations of the quantities of C4d and CR1 present on surfaces of red blood cells in a sample obtained from the same patient in the past.

In both instances, when speaking of "determination" and "quantity," we mean to include both an absolute amount or quantity of material, as well as (in addition, or alternatively), a ratio of C4d to CR1. As will be discussed below, either or both of these measurements can be used, particularly in diagnosing either SLE or scleroderma in a patient.

All publications and patent applications cited in this specification are herein incorporated by reference as if each individual publication or patent application were specifically and individually indicated to be incorporated by reference.

General Procedures

The invention involves conducting assays on blood samples obtained from patients to determine C4d and preferably also CR1.

Samples of blood are obtained from the patient and are treated with EDTA (ethylenediaminetetraacetate) to inhibit complement activation. The samples are maintained at room temperature or under cold conditions. Assays are run preferably within 48 hours.

The determination of C4d and CR1 may be done by a number of methods including flow cytometry, ELISA using red blood cell lysates, and radioimmunoassay. In one embodiment of this invention, the determination of the level of C4d and CR1 is made using flow cytometric methods, with measurements taken by direct or indirect immunofluorescence using polyclonal or monoclonal antibodies specific for each of the two molecules. Each of these two molecules can be measured with a separate sample or using a single sample.

The mean fluorescence channel (MFC) for erythrocyte CR1 and C4d is determined individually. The same type of assay may be used for diagnosis or for monitoring disease activity in patients known to have SLE or scleroderma.

Development of an assay of this type for CR1 and for C4d is known in the art and described in Freysdottir, et al., J. Immunol. Meth. vol. 135, 2005 (1991). That assay was a flow cytometric assay for CR1 and for protein fragments C4d and C3d on erythrocytes, and was described as enabling the identification of individuals having comparatively high or comparatively low levels of CR1. However, erythrocyte C4d and C3d were low and often not detectable above background (limits of detection). These authors suggest a possible use of their assay in providing general information regarding immune complex load or clearing in patients. However, their work was limited to developing the assay for general use. They did not investigate the use or application of their work for diagnosing or monitoring the activity of particular diseases.

Kits

Kits for conducting the assays for both the diagnosing of disease and monitoring of disease activity are a part of this invention. Said kits will use any of the various reagents needed to perform the methods described herein. For example using the immunofluorescence assays, the kits will generally comprise a conjugate of a monoclonal antibody specific for complement component C4d with a fluorescent moiety, and preferably also a conjugate of a monoclonal antibody specific for complement receptor CR1 with a different fluorescent moiety. Additionally, the kits will comprise such other material as may be needed in carrying out assays of this type, for example, buffers, radiolabelled antibodies, colorimeter reagents etc.

The antibodies for use in these methods and kits are known. Hybridomas secreting Anti-CR1 antibodies are available from the American Type Culture Collection in Maryland (ATCC #HB 8592). A general reference is U.S. Pat. No. 4,672,044. Scripps Clinic and Research Foundation, La Jolla, Calif. Anti-C4d antibodies are available from Quidel Corp. in San Diego, Calif. (#A213) and are generally described in Rogers, J., N. Cooper, et al. Complement activation by beta-amyloid in Alzheimer disease. *PNAS* 89:10016-10020, 1992; Schwab, C. et al. Neurofibrillary tangles of Guam Parkinson-dementia are associated with reactive microglia and complement proteins. *Brain Res* 707(2):196 1996; Gemmell, C. A flow cytometric immunoassay to quantify adsorption of complement activation products on artificial surfaces. *J Biomed Mater Res* 37:474-480, 1997; and, Stoltzner, S. E., et al. Temporal accrual of complement proteins in amyloid plaques in patients with Down's syndrome with Alzheimer's disease. *Am J Path* 156:489-499, 2000.

The determination of the C4d and CR1 values may alternatively be conducted using a number of standard measurement techniques such as ELISA. Instead of fluorescent labels, there may be used labels of other types, such as radioactive and colorimetric labels. If such other types of assays are to be used, the kits will comprise monoclonal antibodies specific for C4d and CR1 conjugated with appropriate labels such as radioactive iodine, avidin, biotin or enzymes such as peroxidase.

Diagnostic Methods

Diagnosis of a patient with SLE or scleroderma is carried out by comparing the determination of C4d and preferably also of CR1 with a base value or range of values for the quantities of these entities typically present on the surfaces of red blood cells in normal individuals. In normal individuals, C4d is present in relatively low levels on surfaces of red blood cells. When using flow cytometric measurement with indirect immunofluorescence, the MFC of C4d on red blood cells in healthy individuals ranged from 1.06 to 16.12 (mean 5.7). (Table II and Table VII). The MFC of erythrocyte C4d in patients having SLE was higher than that of healthy individuals and ranged from 2.66 to 155.03 (mean 23.9). (Table III and Table VII). Patients with scleroderma also had elevated levels of C4d as compared to healthy individuals. In patients with scleroderma, the MFC of erythrocyte C4d ranged from 2.86 to 28.89 (mean 11.6). (Table VI and Table V).

Conversely, as is generally known in the art, the level of CR1 on surfaces of erythrocytes of individuals having SLE was usually lower than in healthy individuals. In the latter, the value of the MFC for erythrocyte CR1 ranged from 10.53 to 50.83 (mean 25.4) (Table II and Table VII), whereas the MFC for erythrocyte CR1 from patients having SLE ranged from 1.41 to 40.89 (mean 12.4). (Table III and Table VII). Patients with scleroderma had MFC values for erythrocyte CR1 (range 4.69 to 38.26, mean 18.4) (Table VI and Table VII) that were lower than healthy individuals but higher than those with SLE.

A further indication of a diagnosis of SLE is based on the ratio of erythrocyte CR1 to erythrocyte C4d in these assays. More than 93% of patients with SLE had a CR1:C4d ratio less than 3.00, whereas more than 77% of healthy individuals had a ratio of greater than 3.00. Thus, a ratio of CR1:C4d less than 3.00 in an individual is an indication of SLE.

A further method to distinguish between a diagnosis of SLE and a diagnosis of scleroderma is to compare the erythrocyte CR1:C4d ratios. Greater than 47% of patients with SLE had a CR1:C4d ratio less than 0.69, whereas only one of 30 patients with scleroderma had a CR1:C4d ratio less than 0.69. Thus, a ratio of CR1:C4d less than 0.69 distinguishes SLE from scleroderma.

Monitoring of Patients

A particular feature of the methods of this invention is the ability to monitor the activity of a patient's disease. The life span of a red blood cell is approximately 120 days. Therefore, a particular feature of this assay or method is to indicate or reflect SLE or scleroderma activity that has occurred in the patient during the preceding several weeks or even several months. It is possible, using this procedure, to identify the occurrence of a flare-up of SLE or scleroderma during the previous few weeks or possibly even the previous several months due to persistence of C4d deposited on the surface of red blood cells. The timing of a previous occurrence may be approximated by separating from the sample the C4d-bearing erythrocytes and ascertaining their age by conventional techniques such as density gradient centrifugation (Rennie, C. M., S. Thompson, et al. (1979). Human erythrocyte fractionation in Percoll density gradients. *Clinica Chimica Acta* 98: 119-125).

Also of importance is that the method of this invention is capable of detecting evidence of complement activation in scleroderma, which is a relatively non-inflammatory disease. At the present time, there are no useful circulating markers, or, for that matter, markers of any kind, for measuring disease activity of scleroderma.

Automation and Computer Software

The determinations of C4d and CR1 and the diagnostic and disease activity monitoring methods described above can be carried out manually, but often are conveniently carried out using an automated system and/or equipment, in which the blood sample is analyzed automatically to make the necessary determination or determinations, and the comparison with the base or reference value is carried out automatically, using computer software appropriate to that purpose.

Thus, in one aspect, the invention comprises a method for diagnosing or monitoring systemic lupus erythematosus in an individual comprising (a) automatically determining, in a blood sample from the individual containing red blood cells, complement component C4d and complement receptor CR1 deposited on surfaces of red blood cells in the sample, and (b) automatically comparing said determinations with reference values for component C4d and receptor CR1, respectively, on surfaces of red blood cells. In another aspect this automated method includes one in which the reference values comprise a ratio of C4d:CR1.

The invention also comprises a method for diagnosing or monitoring scleroderma in an individual comprising (a) automatically determining, in a blood sample from the individual containing red blood cells, complement component C4d and complement receptor CR1 deposited on surfaces of red blood cells in the sample, and (b) automatically comparing said determinations with reference values for component C4d and receptor CR1, respectively, on surfaces of red blood cells. In another aspect this automated method also includes one in which the reference values comprise a ratio of C4d:CR1.

Another aspect of the invention comprises a method for diagnosing or monitoring systemic lupus erythematosus in an individual comprising (a) automatically determining, in a blood sample from the individual containing red blood cells, complement component C4d deposited on surfaces of the blood cells in the sample, and (b) automatically comparing said determination with a reference value for component C4d deposited on surfaces of red blood cells.

A further aspect of the invention comprises a method for diagnosing or monitoring scleroderma in an individual comprising (a) automatically determining, in a blood sample from the individual containing red blood cells, complement component C4d deposited on surfaces of red blood cells in the sample, and (b) automatically comparing said determination with a reference value for component C4d deposited on surfaces of red blood cells.

Computer software, or computer-readable media for use in the methods of this invention include:

(1): a computer readable medium, comprising:
  (a) code for receiving data corresponding to a determination of complement component C4d deposited on surfaces of red blood cells;
  (b) code for retrieving a reference value for complement component C4d deposited on surfaces of red blood cells of individuals; and
  (c) code for comparing the data in (a) with the reference value of (b); and (2): a computer readable medium as just described, further comprising:
  (d) code for receiving data corresponding to a determination of complement receptor CR1 deposited on surfaces of red blood cells;
  (e) code for retrieving a range of reference values for complement receptor CR1 deposited on surfaces of red blood cells of individuals; and
  f) code for comparing the data in (d) with the reference values of (e).

In embodiments of the invention, one or more reference values may be stored in a memory associated with a digital computer. After data corresponding to a determination of complement C4d is obtained (e.g., from an appropriate analytical instrument), the digital computer may compare the C4d data with one or more appropriate reference values. After this comparison takes place, the digital computer can automatically determine if the data corresponding to the determination of complement C4d is associated with SLE.

Accordingly, some embodiments of the invention may be embodied by computer code that is executed by a digital computer. The digital computer may be a micro, mini or large frame computer using any standard or specialized operating system such as a Windows™ based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples are provided by way of illustration only and not by way of limitation. Those of skill will readily recognize a variety of noncritical parameters which could be changed or modified to yield essentially similar results.

EXAMPLES AND EXPERIMENTAL DATA

The following examples are provided by way of illustration only and not by way of limitation. Those of skill will readily recognize a variety of noncritical parameters that could be changed or modified to yield essentially similar results.

Example 1

Assays of C4d and CR1 in Healthy Controls: Minimal Fluctuation Over Time

Initially, six healthy individuals were studied. Each of these normal controls was studied on at least two separate days, and one individual was studied on six different days over a span of three months. As shown in Table I, C4d was detected at low levels on erythrocytes of each of the six healthy individuals, and the level of C4d detected was remarkably constant over days, weeks, and even months within a given individual. These data demonstrated that C4d could be easily and reliably detected on erythrocytes of any individual, and the consistent levels observed in healthy individuals indicated that even slight fluctuations reflect disease activity. As expected, CR1 was present at much higher levels than C4d on erythrocytes of all normal individuals, yet CR1 levels also demonstrated minimal fluctuation over days, weeks, and even months.

Samples of 1 mL of EDTA-anticoagulated peripheral blood were taken from each individual and used as a source of red blood cells. The cells were washed and resuspended in FACS buffer. Levels of C4d and CR1 were measured by indirect immunofluorescence using monoclonal antibodies specific for C4d and CR1, respectively, with C4d and CR1 each being measured with a separate sample. Levels of C4d and CR1 are quantitated by flow cytometry using a FACS-Calibur cytometer (Becton Dickinson). The red blood cells were identified by forward and side scatter and the mean fluorescence channel (MFC) was determined individually for C4d and CR1 respectively.

More particularly, blood was collected in 5 cc lavender-topped tubes containing EDTA as an anticoagulant (Becton Dickinson, Franklin Lakes, N.J.). Whole blood was diluted in phosphate buffered saline containing 1% bovine calf serum (PBSB). Erythrocytes were pelleted, washed with PBSB, and aliquotted for antibody staining. Monoclonal antibodies (mAb) were added to erythrocytes at a concentration of 10 μg/ml. The cells were incubated for 20 min at 4° C., and washed with cold PBSB+0.2% sodium azide. A secondary antibody, goat anti-mouse IgG conjugated to fluorescein isothyocyanate (FITC) from Jackson Immunoresearch Laboratories (#115-096-062) was added to cells at a concentration of 10 μg/ml. Cells were incubated and washed as described above, resuspended in PBSB+0.2% sodium azide, and analyzed by flow cytometry using a FACSCalibur (Becton Dickinson Immunocytometry Systems, San Jose, Calif.). Nonspecific binding of immunoglobulins to erythrocytes was determined by performing identical assays in parallel using the isotype control antibody MOPC21 (obtained from ATCC). Specific binding of anti-C4d and anti-CR1 were determined by subtracting the MFC obtained with MOPC21 from the MFC obtained with anti-C4d and anti-CR1 respectively. Sibinovic, K. H., M. Potter, L. D'Hoostelaere, B. Rode, J. Wax. 1976, Catalogue of Plasmacytomas and Other Tumors of the Lymphoreticular System, Third Edition, Litton Bionetics, Inc. p33.

TABLE I

C4d and CR1 on Erythrocytes of Healthy Individuals

| Healthy Individual | Date | C4d | CR1 |
|---|---|---|---|
| 001 | Jul. 12, 2000 | 9.06 | 55.12 |
| 001 | Jul. 13, 2000 | 9.47 | 54.35 |
| 001 | Jul. 14, 2000 | 9.66 | 53.54 |
| 001 | Jul. 20, 2000 | 9.88 | 51.61 |
| 002 | Jul. 13, 2000 | 6.91 | 40.50 |
| 002 | Jul. 20, 2000 | 6.13 | 47.07 |
| 003 | Jul. 14, 2000 | 8.94 | 23.06 |
| 003 | Jul. 20, 2000 | 8.68 | 22.45 |
| 004 | Jul. 14, 2000 | 10.77 | 53.82 |
| 004 | Jul. 20, 2000 | 10.82 | 50.91 |
| 004 | Oct. 9, 2000 | 10.06 | 45.24 |
| 005 | Aug. 30 2000 | 8.36 | 32.42 |
| 005 | Sep. 7, 2000 | 10.31 | 30.49 |
| 005 | Sep. 25, 2000 | 10.06 | 32.99 |
| 005 | Sep. 27, 2000 | 8.77 | 28.51 |
| 005 | Oct. 5, 2000 | 8.63 | 31.02 |
| 005 | Nov. 8, 2000 | 8.88 | 25.83 |
| 006 | Oct. 9, 2000 | 7.04 | 36.47 |
| 006 | Oct. 25, 2000 | 6.84 | 34.20 |
| 006 | Nov. 28, 2000 | 6.85 | 35.24 |

Example 2

Assays of CR1 and C4d to Distinguish Patients with SLE from Healthy Controls

This example describes conducting assays on patients to diagnose systemic lupus erythematosus, and to establish reference values or ranges of values for complement component C4d and complement receptor CR1.

Figure 1B:
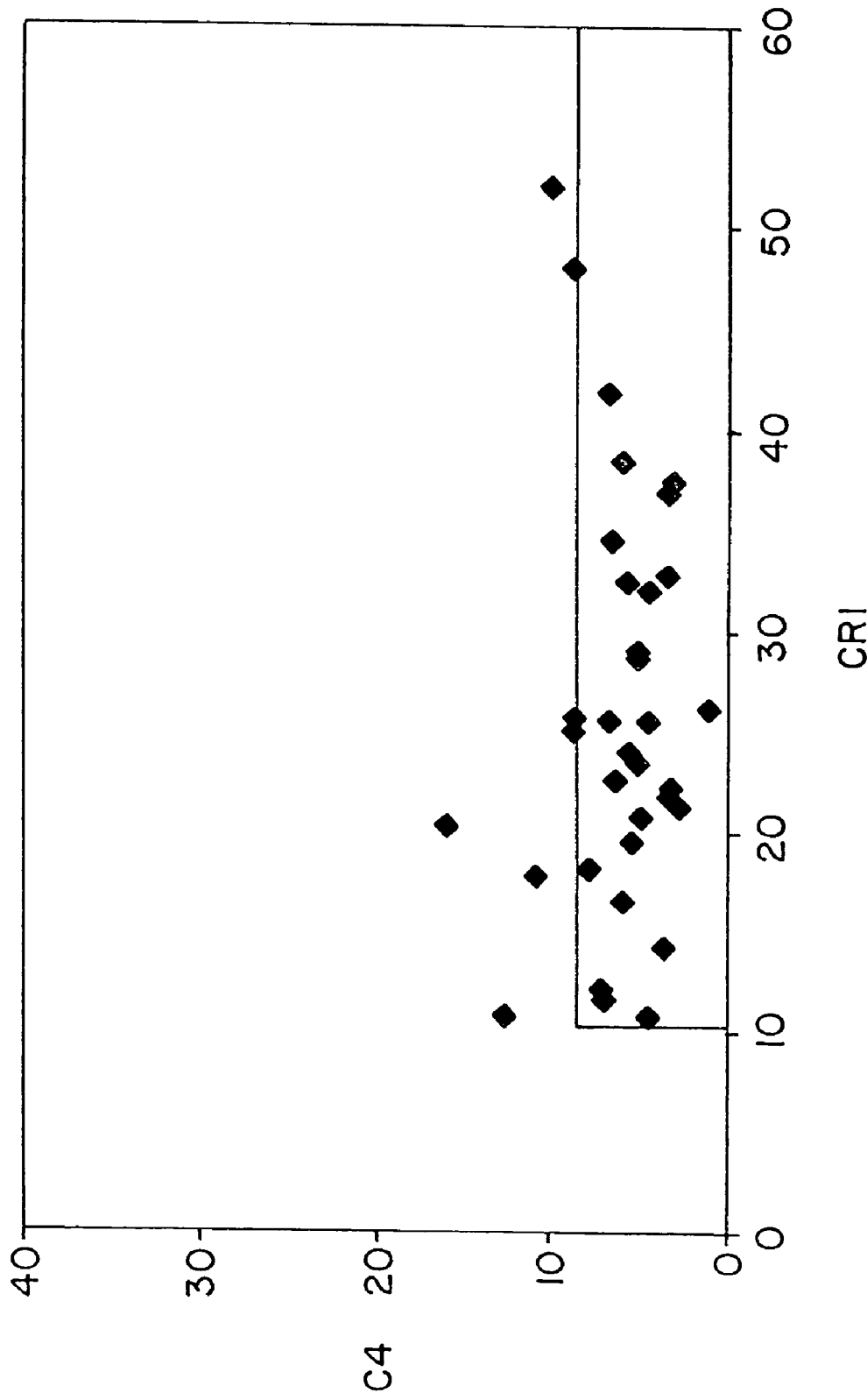

Pilot studies of serial determinations in normal individuals were followed by studies of patients with SLE. For this purpose, we recruited 86 patients with lupus from our outpatient office. A single determination of erythrocyte CR1 and C4d was made, using the same assay, in 86 individuals who met ACR criteria for the diagnosis of SLE (Table III) and in 35 healthy controls (Table II). The mean and median values of CR1 and C4d for patients with SLE and healthy controls are shown in Table VII. Whereas the mean value for C4d in healthy individuals was 5.7, the mean value for C4d among patients with SLE was 23.9 (p=0.0001). The mean MFC for CR1 among the 35 healthy individuals was 25.4, whereas the mean MFC for CR1 in the 86 patients with SLE was 12.4 (p=0.0001). FIGS. 1(a,b) and 2(a,b) present graphs of single specimen determinations of C4d vs. CR1 in the 35 healthy individuals and in the 86 patients with SLE, respectively.

TABLE II

Healthy Controls (n = 35)

| ID | RBC CR1 | RBC C4 |
|---|---|---|
| 2001 | 48.11 | 8.66 |
| 2002 | 36.85 | 3.36 |
| 2003 | 19.55 | 5.43 |
| 2004 | 50.83 | 5.95 |
| 2005 | 38.39 | 5.74 |
| 2006 | 28.98 | 4.92 |
| 2007 | 41.82 | 6.65 |
| 2008 | 32.86 | 3.43 |
| 2009 | 22.26 | 3.11 |
| 2010 | 32.62 | 5.53 |
| 2011 | 20.28 | 16.12 |
| 2012 | 18.08 | 7.86 |
| 2013 | 24.91 | 5.90 |
| 2014 | 19.99 | 6.13 |
| 2015 | 29.34 | 4.46 |
| 2016 | 16.00 | 4.73 |
| 2017 | 34.83 | 2.05 |
| 2018 | 10.53 | 5.49 |
| 2019 | 23.47 | 4.93 |
| 2020 | 16.57 | 4.09 |
| 2021 | 25.76 | 8.52 |
| 2022 | 14.19 | 3.50 |
| 2025 | 10.86 | 12.62 |
| 2026 | 16.55 | 5.89 |
| 2027 | 25.56 | 4.39 |
| 2028 | 23.81 | 5.69 |
| 2029 | 21.27 | 2.81 |
| 2030 | 10.78 | 4.32 |
| 2031 | 17.89 | 10.84 |
| 2032 | 28.70 | 4.94 |
| 2033 | 26.27 | 1.06 |
| 2034 | 32.08 | 4.30 |
| 2035 | 12.46 | 5.64 |
| 2036 | 35.16 | 5.45 |
| 2037 | 23.31 | 5.06 |

TABLE III

SLE Patients (n = 86)

| Patient ID | RBC CR1 | RBC C4 |
|---|---|---|
| 1001 | 5.81 | 25.68 |
| 1002 | 6.98 | 12.87 |
| 1003 | 7.87 | 55.28 |
| 1004 | 14.27 | 155.03 |
| 1005 | 30.60 | 45.00 |
| 1006 | 9.22 | 43.76 |
| 1007 | 40.89 | 13.45 |
| 1008 | 7.18 | 27.00 |
| 1009 | 14.32 | 13.66 |
| 1010 | 12.23 | 33.17 |
| 1011 | 23.93 | 18.65 |
| 1012 | 12.41 | 6.16 |
| 1013 | 12.26 | 20.64 |
| 1014 | 19.18 | 17.74 |
| 1015 | 1.41 | 11.61 |
| 1016 | 4.77 | 16.52 |
| 1017 | 15.87 | 8.92 |
| 1018 | 14.48 | 9.78 |
| 1019 | 15.44 | 10.53 |

TABLE III-continued

SLE Patients (n = 86)

| Patient ID | RBC CR1 | RBC C4 |
|---|---|---|
| 1021 | 17.11 | 11.13 |
| 1022 | 12.19 | 70.62 |
| 1023 | 12.56 | 22.68 |
| 1024 | 13.75 | 13.02 |
| 1025 | 5.20 | 13.65 |
| 1026 | 7.07 | 6.95 |
| 1027 | 6.40 | 6.85 |
| 1029 | 11.27 | 4.14 |
| 1030 | 18.39 | 5.10 |
| 1031 | 6.29 | 25.40 |
| 1032 | 5.67 | 6.53 |
| 1033 | 9.24 | 9.24 |
| 1034 | 12.45 | 8.53 |
| 1035 | 35.40 | 22.65 |
| 1036 | 7.37 | 31.18 |
| 1037 | 19.09 | 11.56 |
| 1038 | 7.10 | 83.70 |
| 1039 | 23.19 | 22.98 |
| 1040 | 20.26 | 7.70 |
| 1041 | 18.82 | 12.02 |
| 1042 | 9.32 | 16.86 |
| 1043 | 19.68 | 9.49 |
| 1044 | 23.86 | 5.46 |
| 1045 | 10.32 | 12.91 |
| 1046 | 17.47 | 8.49 |
| 1047 | 8.84 | 17.76 |
| 1048 | 5.27 | 19.44 |
| 1049 | 13.53 | 10.24 |
| 1050 | 19.54 | 17.51 |
| 1051 | 2.99 | 13.29 |
| 1052 | 10.59 | 12.35 |
| 1053 | 13.94 | 93.05 |
| 1054 | 3.43 | 88.92 |
| 1055 | 19.19 | 30.64 |
| 1056 | 26.33 | 13.39 |
| 1057 | 17.56 | 9.41 |
| 1058 | 6.43 | 14.22 |
| 1059 | 5.62 | 10.26 |
| 1060 | 17.36 | 5.03 |
| 1061 | 11.79 | 21.94 |
| 1062 | 12.83 | 25.85 |
| 1063 | 9.41 | 12.92 |
| 1064 | 5.59 | 27.63 |
| 1065 | 11.07 | 2.73 |
| 1066 | 1.92 | 31.26 |
| 1067 | 18.96 | 10.75 |
| 1068 | 7.65 | 89.64 |
| 1071 | 10.32 | 3.54 |
| 1072 | 5.57 | 4.63 |
| 1073 | 6.82 | 22.05 |
| 1074 | 16.60 | 2.66 |
| 1075 | 11.66 | 11.61 |
| 1076 | 5.87 | 146.43 |
| 1077 | 12.53 | 14.51 |
| 1078 | 4.22 | 9.72 |
| 1079 | 10.50 | 11.85 |
| 1080 | 9.38 | 27.02 |
| 1081 | 14.03 | 27.93 |
| 1082 | 6.57 | 19.94 |
| 1083 | 8.92 | 6.64 |
| 1084 | 21.93 | 9.50 |
| 1085 | 7.91 | 32.65 |
| 1086 | 12.70 | 13.90 |
| 1087 | 5.43 | 67.68 |
| 1089 | 5.12 | 10.63 |
| 1090 | 8.16 | 34.54 |
| 1091 | 11.96 | 6.51 |

Figure 2A:
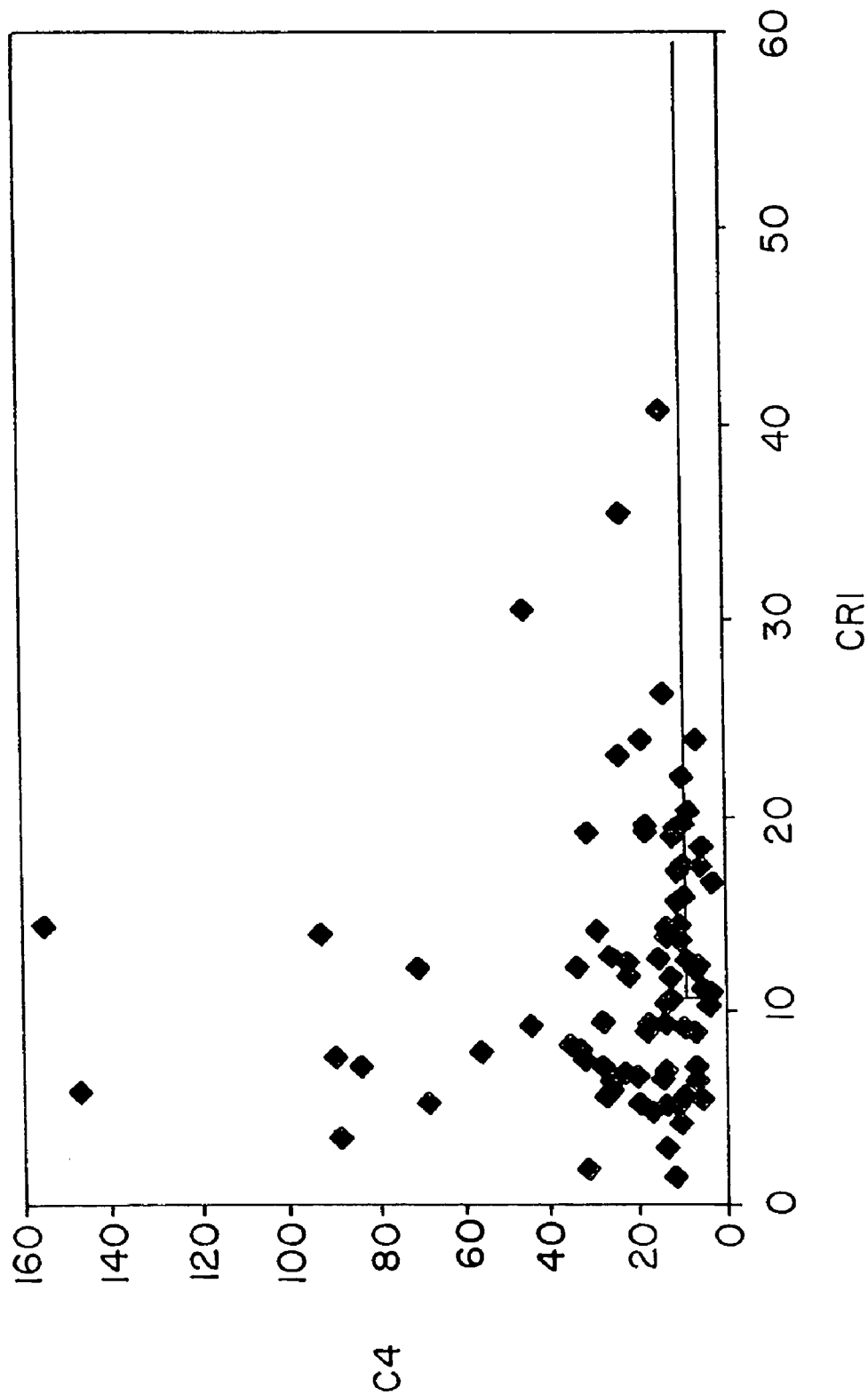
FIGS. 2a and 2b show the same data depicted using two different Y-axes. C4d and CR1 cutpoints, used to differentiate these SLE patients from healthy controls, are shown.
Figure 2B:
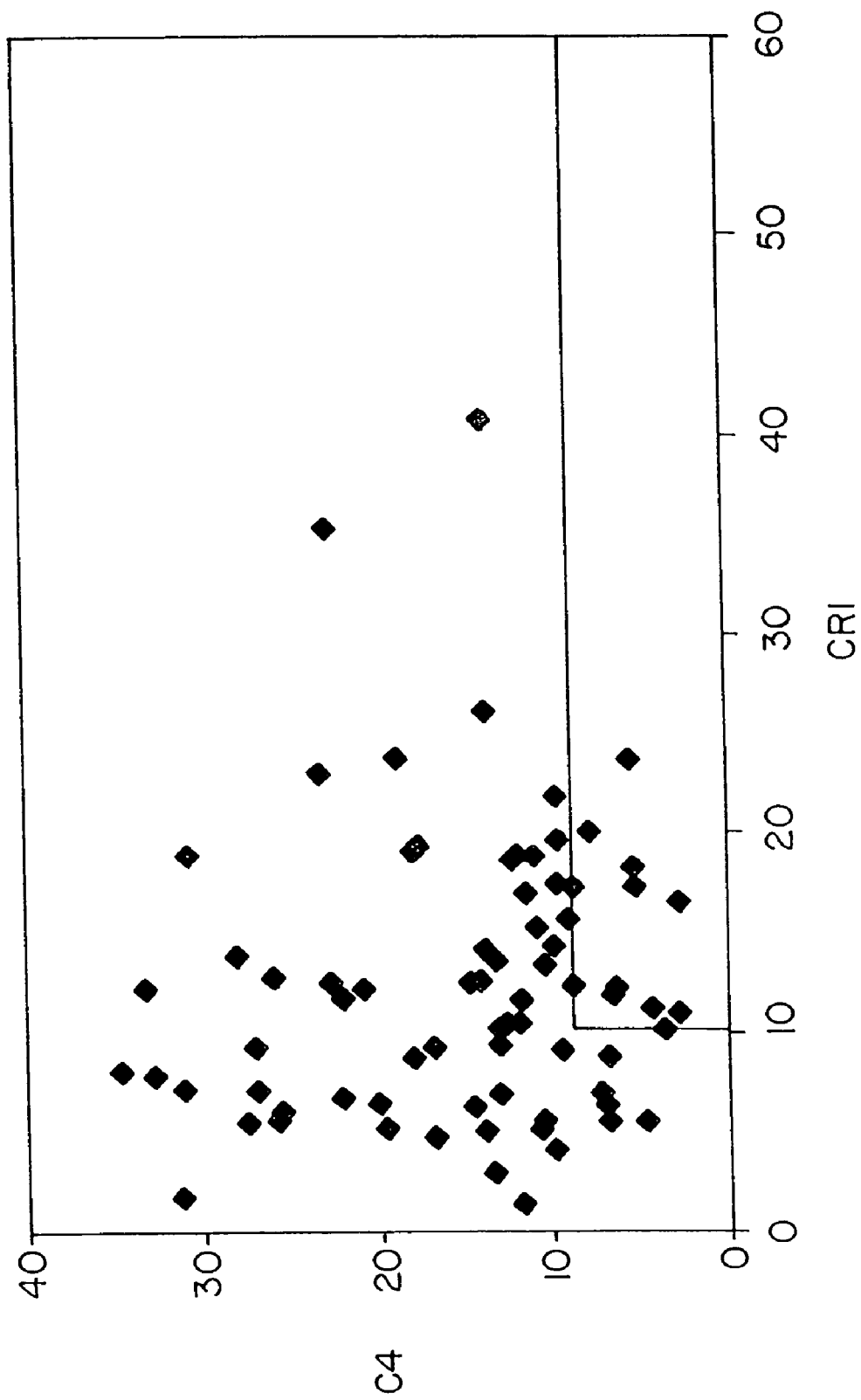

These observations indicated that the combined determinations of erythrocyte CR1 and C4d levels would be a useful diagnostic assay for SLE. Using a CART statistical analysis, we determined the sensitivity and specificity of erythrocyte C4d and CR1 in the diagnosis of SLE using computer-generated cutpoints. Sensitivity is the probability that the assay is positive in a person who has the disease and specificity is the probability that the assay is negative in a person who does not have the disease. These cutpoints are demonstrated in FIGS. 1 and 2 by the solid lines that divide the graphs into four quadrants. These graphs demonstrate that the "lupus profile" that was most commonly observed was a low CR1 and an elevated C4d. In SLE patients compared to healthy controls, the sensitivity and specificity of these measures were 87% and 91%, respectively (Table VIII). The positive predictive values and negative predictive values were also determined. Positive predictive value (PPV) is the likelihood that a person has the disease if the test is positive. The PPV for SLE vs Healthy Controls was 96%. Negative predictive value (NPV) is the likelihood that a person does not have the disease if the test is negative. The NPV for SLE vs Healthy Controls was 74%. No other currently available assay has such high combined PPV and NPV. These data indicate the utility of erythrocyte CR1 and C4 determinations in the diagnosis of SLE Example 3

Figure 3:
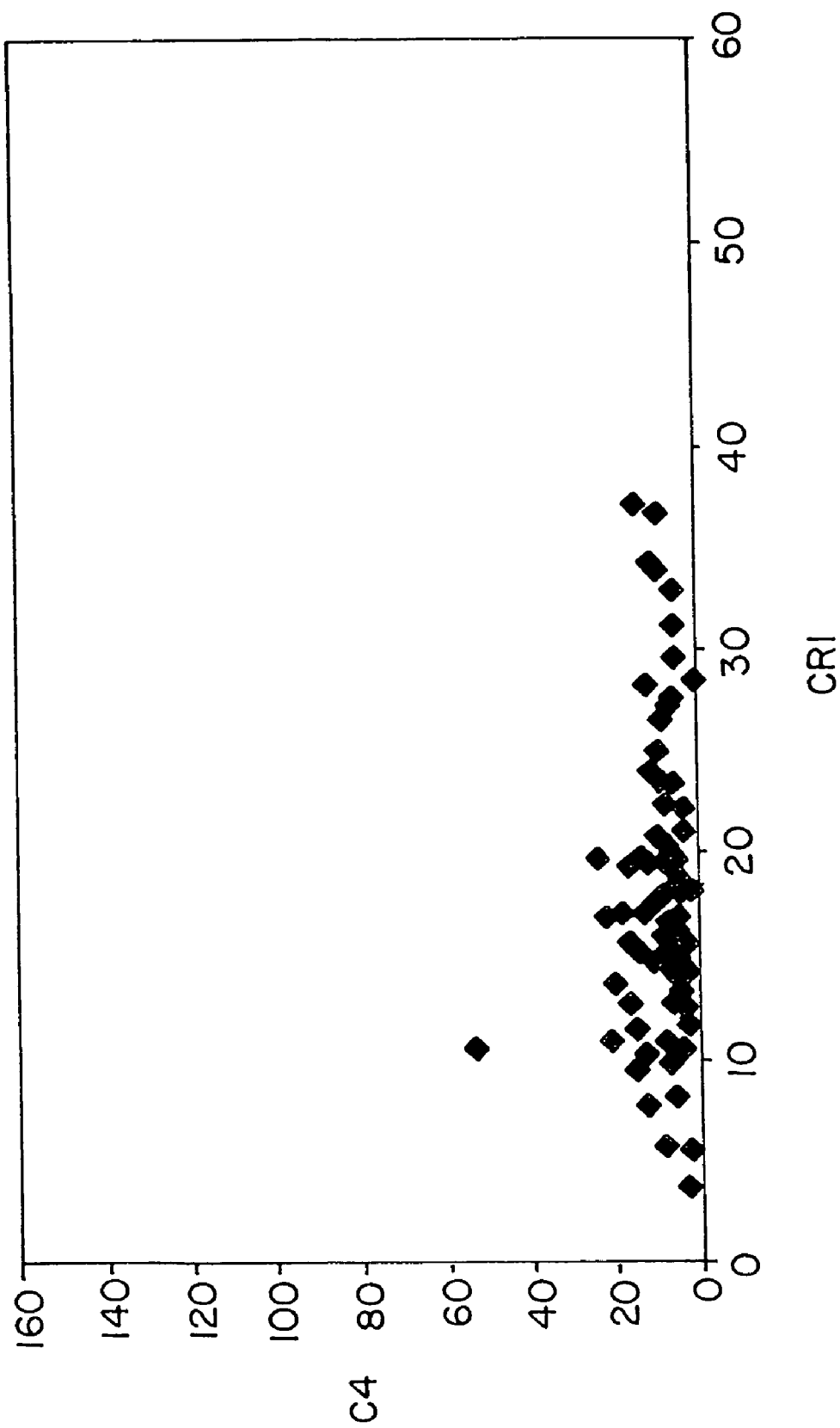
FIG. 3 is a graphical depiction of levels of complement component C4d and complement receptor CR1 on the red blood cells of patients with diseases other than SLE and scleroderma.

Assays of CR1 and C4d for Distinguishing Patients with SLE from Patients with Other Diseases These studies of patients with SLE vs. healthy controls were followed by studies to compare patients with SLE with patients diagnosed with diseases other than SLE (n=111). For these comparison, we studied patients with rheumatoid arthritis (n=15), osteoarthritis (n=2), hepatitis C virus infection (n=17), polymyositis/dermatomyositis (n=33), Wegener's granulomatosis (n=1), Sjogren's syndrome (n=3), sarcoidosis (n=1), urticarial vasculitis (n=1), sickle cell anemia (n=8), overlap syndrome/undifferentiated connective tissue disease (n=15), leukemia/lymphoma (n=9), primary Raynaud's syndrome (n=3), hemophilia (n=2), and psoriatic arthritis (n=1). A single determination of erythrocyte CR1 and C4d was made, using the same assay. The mean and median values of CR1 and C4d for patients with SLE, as compared with patients with other diseases are shown in Table VII. Whereas the mean value for C4d in patients with other diseases was 9.3, the mean value for C4d among patients with SLE was 23.9 (p=0.0001). The mean MFC for CR1 among the 111 patients with other diseases was 18.3, whereas the mean MFC for CR1 in the 86 patients with SLE was 12.4 (p=0.0001). FIG. 3 is a graph of single specimen determinations of C4d vs. CR1 in the 111 patients with other diseases. In SLE patients compared to patients with other diseases, the sensitivity and specificity of these measures were 87% and 89%, respectively (Table VIII). The PPV and NPV were 86% and 90%, respectively. No other currently available test has such high combined probability.

Example 4

Assays of CR1 and C4d for Measuring Disease Activity in Patients with SLE

We then examined the utility of erythrocyte C4d and CR1 levels in measuring disease activity as defined by the Systemic Lupus Activity measure (SLAM). We present the results of the first 86 lupus patients entered into the study. Using a univariate linear regression model, erythrocyte CR1 (p=0.0007) was the only significant predictor of SLAM (Table IV). Serum C3, C4 and anti-dsDNA antibody were not significantly associated with disease activity. In multivariate models, controlling for all variables, erythrocyte CR1 was independently associated with SLAM (p=0.001) (Table V).

Association of anti-ds DNA antibodies with disease activity did not reach statistical significance in this multivariate analysis. These data show that erythrocyte C4d and CR1 determinations provide valuable clinically useful information that is not obtained with traditional "gold standard" measurements of serum C3, serum C4, and anti-dsDNA antibody.

TABLE IV

Association with SLE DiseaseActivity Univariate Analysis

| Variable | P-value |
| --- | --- |
| E-CR1 | 0.0007 |
| E-C4 | 0.6 |
| Serum C3 | 0.93 |
| Serum C4 | 0.81 |
| anti-dsDNA Ab | 0.15 |

TABLE V

Association with SLE Disease Activity Multivariate Analysis

| Variable | P-value |
| --- | --- |
| E-CR1 | 0.001 |
| anti-dsDNA Ab | 0.07 |

Example 5

Use of C4d Determination for the Diagnosis of Scleroderma.

Figure 4:
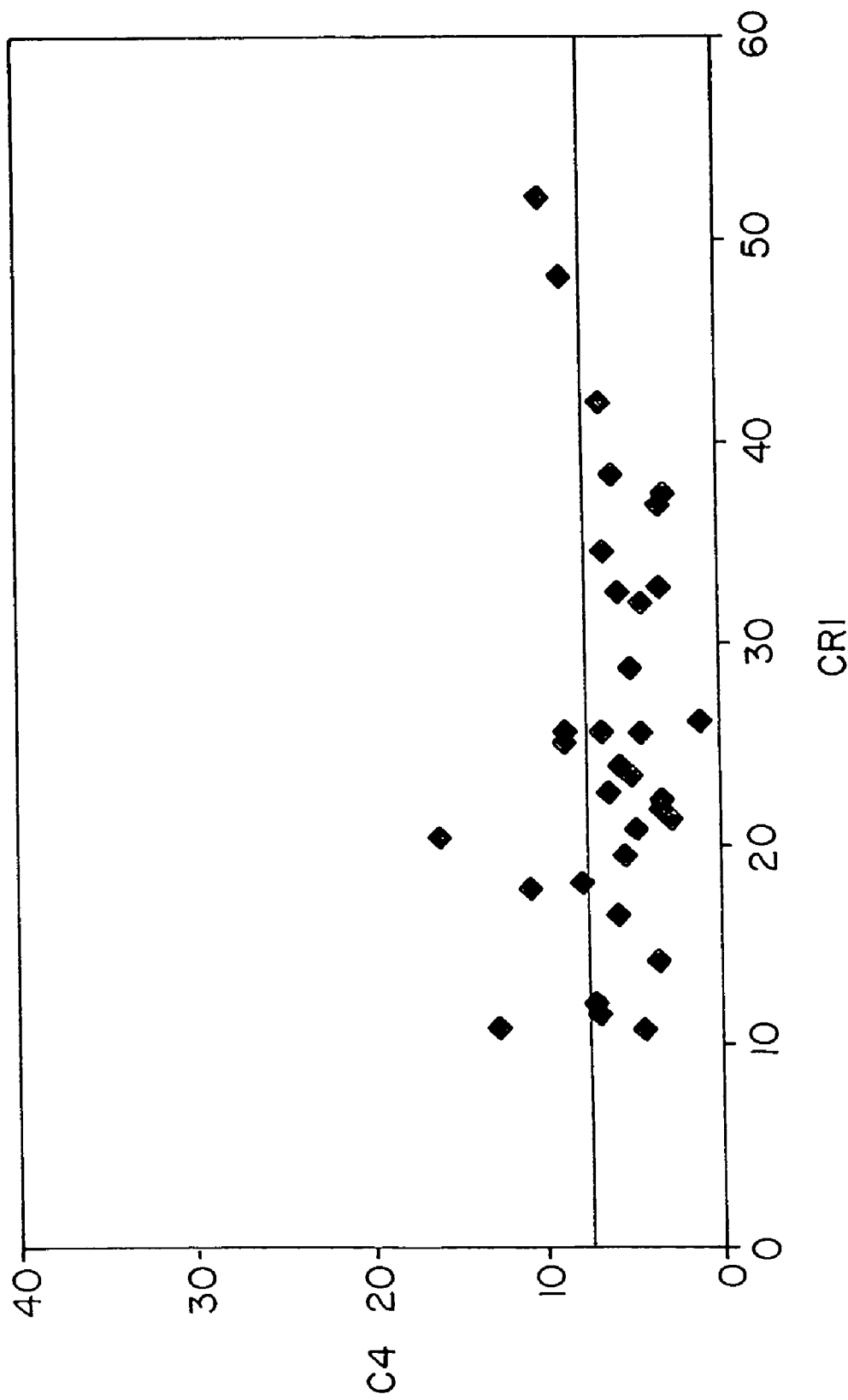
FIG. 4 is a graphical depiction of levels of complement component C4d and complement receptor CR1 on the red blood cells of healthy individuals, i.e. those not having systemic lupus erythematosus, scleroderma or other known diseases. These are the same healthy controls represented in FIG. 1. In this Figure, the C4d cutpoint used to distinguish these healthy controls from patients with scleroderma, is shown. A CR1 cutpoint is not required to distinguish these two groups.
Figure 5:
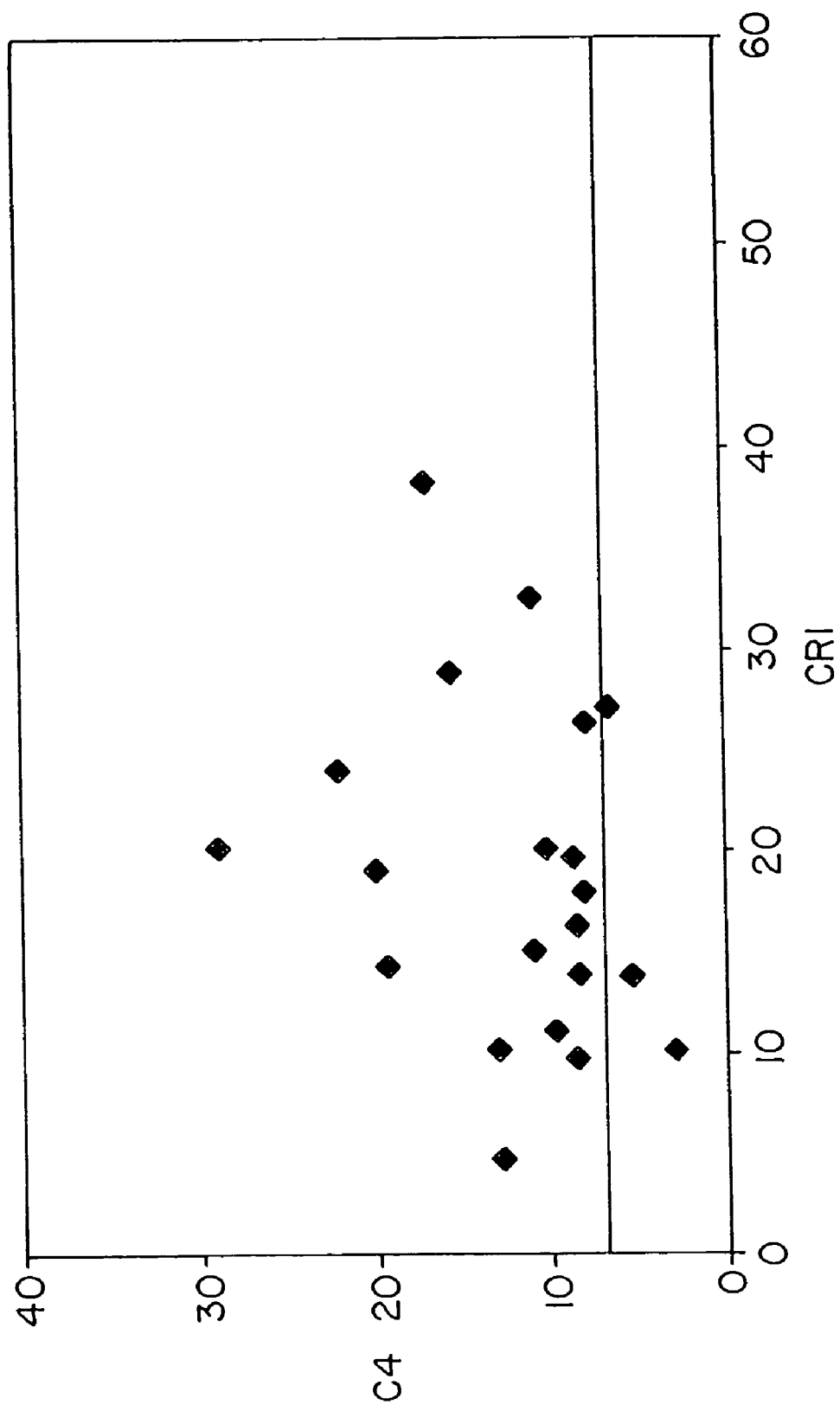
FIG. 5 is a graphical depiction of levels of complement component C4d and complement receptor CR1 on the red blood cells of patients diagnosed as having scleroderma. The C4d cutpoint, used to distinguish these scleroderma patients from healthy controls, is shown.

The same methodology was used to test a sample of 30 scleroderma patients (Table VI) in comparison with the same 35 healthy individuals (Table II). Whereas the mean value for C4d in healthy individuals was 5.7, the mean value for C4d among patients with scleroderma was 11.6 (p=0.0001, Table VII). The mean MFC for CR1 among the 35 normal controls was 25.4, whereas the mean MFC for CR1 in the 30 patients with scleroderma was 18.4 (p=0.0001, Table VII). FIG. 4 is a graph of single specimen determinations of C4d vs. CR1 35 in healthy individuals. FIG. 5 is a graph of single specimen determinations of C4d vs. CR1 in the 30 patients with scleroderma.

TABLE VI

Scleroderma Patients (n = 30)

| Patient ID | RBC CRI | RBC C4 |
| --- | --- | --- |
| 3001 | 38.26 | 16.77 |
| 3002 | 10.97 | 9.71 |
| 3003 | 28.77 | 15.33 |
| 3004 | 17.85 | 7.96 |
| 3006 | 23.95 | 22.12 |
| 3008 | 16.26 | 8.41 |
| 3009 | 18.92 | 19.95 |
| 3010 | 15.12 | 10.80 |
| 3011 | 27.05 | 6.37 |
| 3012 | 32.42 | 10.74 |
| 3013 | 9.62 | 8.46 |
| 3014 | 10.03 | 12.87 |
| 3017 | 19.69 | 8.51 |
| 3019 | 13.93 | 5.38 |
| 3020 | 13.79 | 8.25 |
| 3021 | 26.40 | 7.82 |
| 3022 | 13.67 | 5.26 |
| 3023 | 10.06 | 2.86 |
| 3024 | 20.02 | 28.89 |
| 3025 | 14.32 | 19.30 |
| 3026 | 4.69 | 12.73 |
| 3027 | 20.06 | 9.98 |
| 3028 | 25.37 | 6.15 |
| 3029 | 15.3 | 6.66 |
| 3030 | 19.2 | 8.00 |
| 3031 | 21.28 | 26.12 |
| 3032 | 11.80 | 13.70 |
| 3034 | 11.13 | 5.78 |
| 3035 | 24.19 | 17.00 |
| 3036 | 19.3 | 5.84 |

TABLE VII

Analysis of RBC-CR1 and RBC-C4

| | | RBC-CRI | | | RBC-C4d | | |
| --- | --- | --- | --- | --- | --- | --- | --- |
| | | Mean | Standard Deviation | Median | Mean | Standard Deviation | Median |
| SLE | (n = 86) | 12.4 | 7.2 | 11.5 | 23.9 | 27.9 | 13.6 |
| Scleroderma | (n = 30) | 18.4 | 7.5 | 18.4 | 11.6 | 6.5 | 9.1 |
| Healthy Controls | (n = 35) | 25.4 | 10.2 | 23.8 | 5.7 | 2.9 | 5.4 |
| Other Diseases | (n = 111) | 18.3 | 7.3 | 17.3 | 9.3 | 6.8 | 8.0 |

RBC CR1 and C4 are not normally distributed in any of the comparisons. Therefore, Wilcoxon rank sum test was used.

| Comparison - | CRI (p values) | C4 (p values) |
| --- | --- | --- |
| SLE vs Healthy Controls | 0.0001 | 0.0001 |
| SLE vs Other Diseases | 0.0001 | 0.0001 |
| SLE vs Scleroderma | 0.0001 | 0.004 |
| Scleroderma vs Healthy Controls | 0.004 | 0.0001 |

Using a CART statistical analysis, we determined the sensitivity and specificity of erythrocyte C4d and CR1 in the diagnosis of scleroderma using computer-generated cut-points. In scleroderma patients compared to healthy controls, the sensitivity and specificity of these measures was 83% and 80%, respectively (Table VIII) The positive predictive values and negative predictive values were also determined. The PPV for distinguishing patients with scleroderma from healthy controls was 78%. The NPV for distinguishing patients with scleroderma from healthy controls was 85%. There is no single laboratory test currently used with equivalent sensitivity and specificity, PPV, and NPV for scleroderma.

TABLE VIII

CART Analysis of RBC-CRI and RBC-C4d

| Comparison | Sensitivity | Specificity | PPV | NPV |
|---|---|---|---|---|
| SLE vs. Healthy Control | .87 | .91 | .96 | .74 |
| SLE vs. Other Diseases | .87 | .89 | .86 | .90 |
| Scleroderma vs. Healthy Controls | .83 | .80 | .78 | .85 |

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for diagnosing systemic lupus erythematosus in an individual, comprising:
 (a) detecting, in a blood sample from the individual containing red blood cells, quantities of complement component C4d and complement receptor CR1 both of which are on surfaces of the red blood cells in the sample,
 (b) comparing said quantities with, respectively, the quantities of component C4d and receptor CR1 both on surfaces of red blood cells in samples from individuals not having systemic lupus erythematosus, and
 (c) diagnosing systemic lupus erythematosus in the individual by observing a significantly increased quantity in complement component C4d on surfaces of red blood cells and a significantly decreased quantity of receptor CR1 on surfaces of red blood cells in said sample from the individual compared to said samples from said individuals not having systemic lupus erythematosus.

2. The method according to claim 1 in which step (b) comprises comparing the ratio of C4d:CR1 on surfaces of red blood cells in the sample with the ratio of C4d:CR1 on surfaces of red blood cells of individuals not having systemic lupus erythematosus, wherein a significantly higher ratio of C4d:CR1 on surfaces of red blood cells in the sample with the ratio of C4d:CR1 on surfaces of red blood cells of individuals not having systemic lupus erythematosus is indicative of a diagnosis of systemic lupus erythematosus.

3. The method according to claim 1, in which the detection of C4d and CR1 are conducted by a method comprising binding the C4d to a conjugate of a monoclonal antibody specific for component C4d with a first labeled moiety, binding the CR1 to a conjugate of a monoclonal antibody specific for CR1 with a second labeled moiety, and determining the first and second labeled moieties.

4. The method according to claim 3, in which the labeled moieties are fluorescent moieties.

5. The method according to claim 4 in which the fluorescent moieties are determined by determining the mean fluorescence channel using flow cytometric analysis.

6. A method of monitoring disease activity of systemic lupus erythematosus in an individual, comprising:
 (a) detecting, in a blood sample from the individual containing red blood cells, quantities of complement component C4d and complement receptor CR1 both of which are on surfaces of the red blood cells in the sample,
 (b) comparing said quantities with, respectively, the quantities of component C4d and receptor CR1 both on surfaces of red blood cells in a sample previously obtained from the individual, and
 (c) monitoring disease activity of systemic lupus erythematosus in the individual by observing a change in said quantities of complement component C4d on surfaces of red blood cells and complement receptor CR1 on surfaces of the red blood cells in said sample compared to said sample previously obtained from the individual, wherein systemic lupus erythematosus disease activity in said individual is indicated by a significantly increased quantity in complement component C4d on surfaces of red blood cells and a significantly decreased quantity of complement receptor CR1 on surfaces of red blood cells in said sample from the individual compared to said sample previously obtained from the individual.

7. The method according to claim 6, in which step (b) comprises comparing the ratio of C4d:CR1 on surfaces of red blood cells in the sample with the ratio of C4d:CR1 on surfaces of red blood cells previously obtained from the individual, wherein a significantly higher ratio of C4d:CR1 on surfaces of red blood cells in the sample compared to the sample previously obtained from the individual is indicative of systemic lupus erythematosus disease activity.

8. The method according to claim 6, in which the detection of C4d and CR1 is conducted by a method comprising binding the C4d to a conjugate of a monoclonal antibody specific for C4d with a first labeled moiety, binding the CR1 to a conjugate of a monoclonal antibody specific for CR1 with a second labeled moiety, and determining the first and second labeled moieties.

9. The method according to claim 8, in which the labeled moieties are fluorescent moieties.

10. The method according to claim 9 in which the fluorescent moieties are determined by determining the mean fluorescence channel using flow cytometric analysis.

11. A method of diagnosing systemic lupus erythematosus in an individual, comprising:
 (a) detecting, in a blood sample from the individual containing red blood cells, a quantity of complement component C4d on surfaces of red blood cells in the sample,
 (b) comparing said quantity with the quantity of component C4d on surfaces of red blood cells in samples from individuals not having systemic lupus erythematosus, and
 (c) diagnosing systemic lupus erythematosus in the individual by observing a significantly increased quantity in complement component C4d on surfaces of red blood cells in said sample from the individual compared to said samples from individuals not having systemic lupus erythematosus.

12. The method according to claim 11, in which the detection of C4d is conducted by a method comprising binding the C4d to a conjugate of a monoclonal antibody specific for C4d with a labeled moiety, and determining the labeled moiety.

13. The method according to claim 12, in which the labeled moiety is a fluorescent moiety.

14. The method according to claim 13, in which the fluorescent moiety is determined by determining the mean fluorescence channel using flow cytometric analysis.

15. A method of monitoring disease activity of systemic lupus erythematosus in an individual, comprising:

(a) detecting, in a blood sample from the individual containing red blood cells, a quantity of complement component C4d on surfaces of the red blood cells in the sample, (b) comparing said quantity with the quantity of component C4d on surfaces of red blood cells in a sample previously obtained from the individual, and (c) monitoring disease activity of systemic lupus erythematosus in the individual by observing a change in the quantity of complement component C4d on surfaces of the red blood cells in said sample, wherein systemic lupus erythematosus disease activity in said individual is indicated by a significantly increased quantity in complement component C4d on surfaces of red blood cells in said sample from the individual compared to said sample previously obtained from the individual.

16. The method according to claim 15, in which the detection of C4d is conducted by a method comprising binding the C4d to a conjugate of a monoclonal antibody specific for C4d with a labeled moiety, and determining the first labeled moiety.

17. The method according to claim 16, in which the labeled moiety is a fluorescent moiety.

18. The method according to claim 17 in which the fluorescent moiety is determined by determining the mean fluorescence channel using flow cytometric analysis.

19. A method for diagnosing or monitoring systemic lupus erythematosus in an individual, comprising:

(a) automatically detecting, in a blood sample from the individual containing red blood cells, quantities of complement component C4d and complement receptor CR1, both of which are on surfaces of the red blood cells in the sample, (b) automatically comparing said quantities with reference values for component C4d and receptor CR1, respectively, both on surfaces of red blood cells, and (c) diagnosing systemic lupus erythematosus in the individual by observing a significantly increased quantity in complement component C4d on surfaces of red blood cells and a significantly decreased quantity of receptor CR1 on surfaces of red blood cells in said sample from the individual compared to said reference values; or (d) monitoring disease activity of systemic lupus erythematosus in the individual by observing a change in said quantities of complement component C4d on surfaces of red blood cells and complement receptor CR1 on surfaces of the red blood cells in said sample compared to said reference values, wherein systemic lupus erythematosus disease activity in said individual is indicated by a significantly increased quantity in complement component C4d on surfaces of red blood cells and a significantly decreased quantity of complement receptor CR1 on surfaces of red blood cells in said sample from the individual compared to said reference values.

20. The method according to claim 19, in which the reference values comprise a ratio of C4d:CR1, and wherein a significantly higher ratio of C4d:CR1 on surfaces of red blood cells in the sample from the individual compared to the reference value ratio of C4d:CR1 is indicative of a diagnosis of systemic lupus erythematosus or is indicative of systemic lupus erythematosus disease activity in an individual with systemic lupus erythematosus.

21. A method for diagnosing or monitoring systemic lupus erythematosus in an individual, comprising:

(a) automatically detecting, in a blood sample from the individual containing red blood cells, a quantity of complement component C4d on surfaces of the red blood cells in the sample, (b) automatically comparing said quantity with a reference value for component C4d on surfaces of red blood cells, and (c) diagnosing systemic lupus erythematosus in the individual by observing a significantly increased quantity in complement component C4d on surfaces of red blood cells in said sample from the individual compared to said reference values; or (d) monitoring disease activity of systemic lupus erythematosus in the individual by observing a change in the quantity of complement component C4d on surfaces of the red blood cells in said sample compared to said reference values, wherein systemic lupus erythematosus disease activity in the individual is indicated by a significantly increased quantity in complement component C4d on surfaces of red blood cells in said sample from the individual compared to said reference values.

* * * * *

UNITED STATES PATENT AND TRADEMARK OFFICE
CERTIFICATE OF CORRECTION

PATENT NO. : 7,390,631 B2 Page 1 of 1
APPLICATION NO. : 10/489219
DATED : June 24, 2008
INVENTOR(S) : Joseph M. Ahearn et al.

It is certified that error appears in the above-identified patent and that said Letters Patent is hereby corrected as shown below:

Column 15, line 64, "CR1 35 in" should be --CR1 in 35--.

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,390,631 B2  
APPLICATION NO. : 10/489219  
DATED : June 24, 2008  
INVENTOR(S) : Ahearn and Manzi Page 1 of 1

It is certified that error appears in the above-identified patent and that said Letters Patent is hereby corrected as shown below:

<u>In the Specification:</u>

Column 1, lines 15-17, "Certain work described herein was supported by Grant No. N01AR92239 between the NIH and University of Pittsburgh. The Government may have certain rights in this invention" should read -- This invention was made with government support under grant no. N01AR92239, grant no. RO1HL-074335, grant no. RO1AR-4676402, grant no. RO1AR-46588, grant no. MO1-RR-00056, and grant no. K23 AR-051044, awarded by the National Institutes of Health. This invention was made with government support under grant no. K24 AR-02213 and grant no. MO1-RR 00056, awarded by the National Center for Research Resources. The government has certain rights in the invention. --.

Signed and Sealed this  
Seventeenth Day of December, 2013

Margaret A. Focarino  
*Commissioner for Patents of the United States Patent and Trademark Office*